(12) United States Patent
Roberson, Jr. et al.

(10) Patent No.: US 7,267,124 B1
(45) Date of Patent: Sep. 11, 2007

(54) EMERGENCY TRACHEOSTOMY KIT

(76) Inventors: Travis Hubert Roberson, Jr., 103 Crestview, P.O. Box 218, Church Hill, TN (US) 37642; Charlie J. Smith, 135 River Bridge Rd., Kingsport, TN (US) 37663-3833

( * ) Notice: Subject to any disclaimer, the term of this patent is extended or adjusted under 35 U.S.C. 154(b) by 0 days.

(21) Appl. No.: 11/349,410

(22) Filed: Feb. 7, 2006

(51) Int. Cl.
*A61M 16/00* (2006.01)

(52) U.S. Cl. .................. 128/207.29; 604/116

(58) Field of Classification Search .......... 128/207.14, 128/207.29; 623/9; 604/161, 164.01, 116; 606/167, 172
See application file for complete search history.

(56) References Cited

U.S. PATENT DOCUMENTS

| | | | |
|---|---|---|---|
| 2,786,469 A | 3/1957 | Cohen | |
| 2,898,917 A | 8/1959 | Wallace | |
| 3,306,297 A | 2/1967 | Voorhees et al. | |
| 3,307,551 A | 3/1967 | Violet, Jr. | |
| 3,415,250 A | 12/1968 | Peterson | |
| 3,476,113 A | 11/1969 | Tarsitano | |
| 3,613,684 A | 10/1971 | Sheridan | |
| 3,683,911 A | 8/1972 | McCormick | |
| 3,791,386 A | 2/1974 | McDonald | |
| 3,841,334 A | 10/1974 | Wolf | |
| 3,892,038 A | 7/1975 | Novak | |
| 3,898,735 A | 8/1975 | Himeno | |
| 3,981,398 A | 9/1976 | Boshoff | |
| 4,291,690 A | 9/1981 | Jessen | |
| 4,324,044 A | 4/1982 | Shahinian, Jr. | |
| 4,331,138 A | 5/1982 | Jessen | |
| 4,332,245 A | 6/1982 | Boone, Sr. | |
| 4,438,768 A | 3/1984 | Barrickman | |
| 4,541,427 A * | 9/1985 | Koss | 128/207.29 |
| 4,569,133 A | 2/1986 | Schmidt | |
| 4,570,628 A * | 2/1986 | Neal | 128/853 |
| 4,632,112 A | 12/1986 | Matthews | |
| 4,717,385 A | 1/1988 | Cameron et al. | |
| 4,759,363 A | 7/1988 | Jensen | |
| 4,941,882 A | 7/1990 | Ward et al. | |
| 4,985,019 A | 1/1991 | Michelson | |
| 5,073,169 A | 12/1991 | Raiken | |
| 5,135,506 A | 8/1992 | Gentelia et al. | |
| 5,188,100 A | 2/1993 | Miles et al. | |
| 5,224,935 A | 7/1993 | Hollands | |
| 5,336,206 A | 8/1994 | Shichman | |
| 5,370,625 A | 12/1994 | Shichman | |
| 5,507,279 A * | 4/1996 | Fortune et al. | 128/200.26 |
| 5,558,081 A | 9/1996 | Lipkin | |
| 5,819,734 A | 10/1998 | Deily et al. | |
| 5,957,978 A * | 9/1999 | Blom | 623/9 |
| 6,105,577 A | 8/2000 | Varner | |

FOREIGN PATENT DOCUMENTS

WO WO85/01431 4/1985

* cited by examiner

*Primary Examiner*—Steven O. Douglas
(74) *Attorney, Agent, or Firm*—Luedeka, Neely & Graham PC

(57) ABSTRACT

A kit that facilitates performance of a tracheostomy in emergency situations remote from an operating room. The kit includes a template guide for placement on a person on which the tracheostomy is to be performed to indicate the desired incision location, a cutting instrument configured for making an incision of a desired depth, and a breathing tube for placement into the incision.

6 Claims, 1 Drawing Sheet

EMERGENCY TRACHEOSTOMY KIT

FIELD OF THE INVENTION

This invention relates generally to surgical kits More particularly, this invention relates to an emergency tracheostomy kit.

BACKGROUND AND SUMMARY OF THE INVENTION

Tracheostomy is a surgical procedure for providing an alternate breathing pathway by cutting an opening in the trachea or windpipe through the neck. While typically performed in an operating room by a surgeon, such procedures are often indicated in emergency situations, such as when a person is choking because their windpipe has been blocked by food, blood, or other substances. Tracheotomy refers to the act of making an opening, called a stoma, in the trachea. A tube is inserted into the stoma to provide an air passage.

While trained medical personnel have skill and knowledge relating to tracheostomy procedures, a tracheostomy may be needed in emergency situations remote from emergency rooms and trained personnel. For such situations, guidance as to the desired location and depth of an incision is important to the performance of the procedure.

Accordingly, the disclosure relates to a kit that facilitates performance of a tracheostomy in emergency situations remote from an operating room. In a preferred embodiment, the kit includes a guide configured for placement adjacent a collarbone area of a patient to indicate a desired incision location; a cutting instrument for making an incision at the desired incision location; and a conduit configured for placement a desired depth within the incision.

BRIEF DESCRIPTION OF THE DRAWINGS

Further features of preferred embodiments of the invention will become apparent by reference to the detailed description of preferred embodiments when considered in conjunction with the figures, which are not to scale, wherein like reference numbers, indicate like elements through the several views, and wherein.

DETAILED DESCRIPTION

With reference to the drawings, the disclosure relates to a kit that facilitates performance of a tracheostomy in emergency situations remote from an operating room. In a preferred embodiment, the kit includes a template guide 10 for placement on a person on which the tracheostomy is to be performed to indicate the desired incision location, a cutting instrument 12 configured for making an incision of a desired depth, and a breathing tube 14 for placement into the incision. The kit may be provided as by providing the guide 10, cutting instrument 12, and tube 14 together in a container, preferably with drawings and instructions showing use thereof in the performance of a tracheostomy. The kit may also include other components, such as an alcohol preparation pad for cleaning of the incision site.

Figure 1:
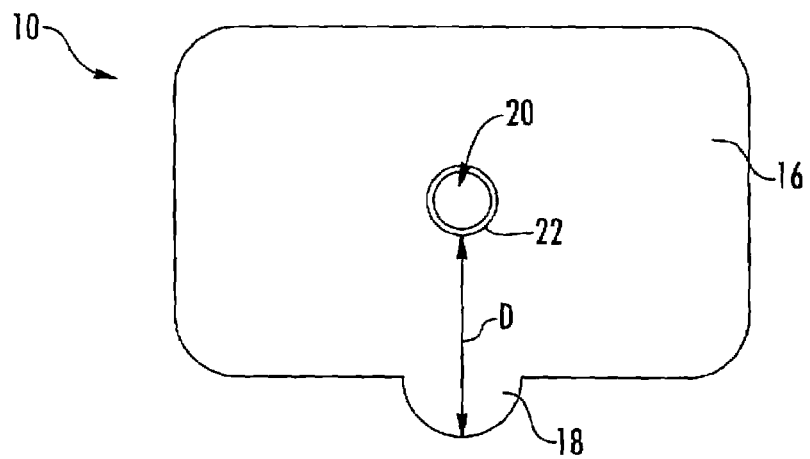
FIG. 1 is a top plan view of a template guide component of a tracheostomy kit according to a preferred embodiment.
Figure 2:
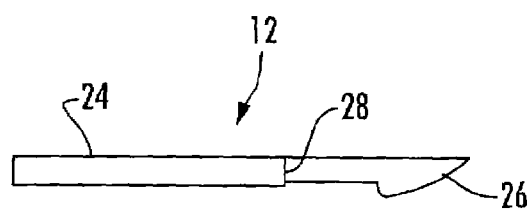
FIG. 2 is a side view of a cutting instrument component of a tracheostomy kit according to a preferred embodiment.
Figure 3:
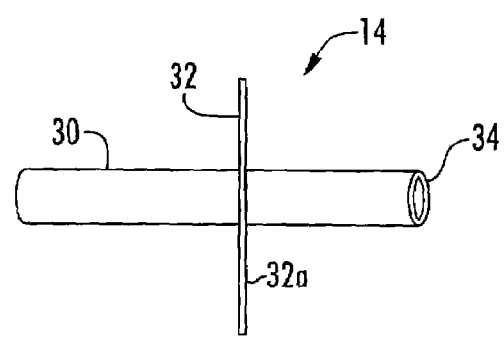
FIG. 3 is a top plan view of a breathing tube component of a tracheostomy kit according to a preferred embodiment.

With reference to FIG. 1, the template guide 10 is preferably provided as by an adhesive-backed substrate 16 configured for placement adjacent a collarbone area of a patient to indicate the desired incision location. For example, the substrate 16 is preferably substantially rectangular or square, but including a flange 18 extending from a side thereof. The flange 18 is configured to be received at the collarbone connection of a person, which is located at the base of the front of the neck.

To mark a desired incision location, the guide 10 includes an aperture 20. The aperture 20 is located on the substrate 16 so that when the guide 10 is positioned with the flange 18 at the collarbone connection of a patient, the aperture 20 overlies the desired incision site. The aperture 20 is preferably defined by a metal ring 22 secured to the substrate 16 to limit the incision to the desired site within the ring. The ring 22 is preferably circular, but may be of other shape, such as an elongate slot or other shape corresponding to a desired incision shape.

The substrate 16 may be provided as by a relatively flexible but strong paperboard or plastic sheet material. A lower surface of the substrate 16 preferably includes an adhesive coating covered by release strips, with the substrate and the other components of the kit each packaged in a sterile tear-off wrapper.

For the purpose of example, for adult usage, the guide 10 preferably has a length of about 2½ inches and a width of about 2 inches, with the aperture 20 being centrally located with a diameter of about 5/16 inch, such that the distance D shown in FIG. 1 is about 1¼ inches.

The cutting instrument 12 is preferably a disposable scalpel having a handle 24 and a blade 26. To facilitate the making of an incision of desired depth, the instrument 12 preferably includes indicia 28 thereon at a location relative to the tip of the blade 26 that corresponds to a desired depth of cut for making an incision. The indicia 28 may be a line or other visual marking or a projection or a stop or other structure to limit the depth of incision. Thus, the indicia 28 is configured to visually indicate or physically limit the penetration of the blade 26 to a desired depth. For example, a desired depth may be about 1½ inches.

The breathing tube 14 is preferably provided by a conduit such as a cylinder 30 having a stop 32 or other structure attached thereto to position the tube 14 at a desired depth within the incision. The cylinder 30 is preferably made of plastic. The stop 32 is preferably provided as by an adhesive strip with a peel-off covering over an adhesive surface 32a. The use of an adhesive strip is advantageous for securing the tube 14 in the desired position relative to the guide 10. To provide the desired insertion depth of the tube 14, the distance from the stop 32 to inserted end 34 of the cylinder 30 is preferably about 1½ inches. The cylinder preferably has an overall length of about 3½ inches and a diameter of about 3/16.

To use the kit provided by the above-described components, a user first removes the peel-off strips from the substrate 16 and positions the flange 18 at the collarbone connection of the person on whom the tracheostomy is performed. Gentle pressure is applied to the substrate to press the adhesive surface against the skin to maintain the substrate 16 in place. Next, the blade 26 of the cutting instrument is positioned within the aperture 20 and an incision is made to the desired depth defined by the indicia 28. To install the breathing tube 14, the peel-off covering is removed to expose the adhesive surface 32a and the end 34 of the cylinder 30 of the breathing tube 14 is inserted into the incision to a depth as limited by the stop 32 contacting the substrate 16. The adhesive surface 32*a* is then secured to the upper surface of the substrate to secure the cylinder 30 in the desired position and to seal around the cylinder 30 and completing the emergency tracheostomy procedure.

The foregoing description of certain exemplary embodiments of the present invention has been provided for purposes of illustration only, and it is understood that numerous modifications or alterations may be made in and to the illustrated embodiments without departing from the spirit and scope of the invention as defined in the following claims.

What is claimed is:

1. A kit that facilitates performance of a tracheostomy in emergency situations remote from an operating room and trained personnel, the kit comprising:

a guide configured for being secured adjacent a collarbone connection area of a patient during the performance of the tracheostomy, the guide including an outwardly extending flange configured for being received by the collarbone connection to facilitate placement of the guide at the desired location and an aperture extending through and located on the guide to indicate a desired incision location, the aperture being configured to include structure to limit the incision to the desired site within the aperture;

a cutting instrument for making an incision at the desired incision location; and a conduit configured for placement through the aperture of the guide to a desired depth within the incision, the conduit including a stop configured to contact the substrate to limit passage of the conduit through the aperture of the guide and position the conduit at a desired depth within the incision.

2. The kit of claim 1, wherein the structure to limit the incision comprises a ring surrounding the aperture for limiting the incision to locations within the ring.

3. The kit of claim 1, wherein the cutting instrument includes indicia corresponding to a desired depth of cut for making the incision.

4. The kit of claim 1, wherein the indicia comprises visual indicia.

5. The kit of claim 1, wherein the indicia comprises structure to limit the depth of incision.

6. The kit of claim 1, wherein the conduit comprises a tube having an adhesive strip attached thereto configured for securement to the guide when the tube is installed during performance of an emergency tracheostomy to secure the tube in the desired position and to seal around the tube.

\* \* \* \* \*

UNITED STATES PATENT AND TRADEMARK OFFICE
CERTIFICATE OF CORRECTION

PATENT NO. : 7,267,124 B1  
APPLICATION NO. : 11/349410  
DATED : September 11, 2007  
INVENTOR(S) : Travis Hubert Roberson, Jr. and Charlie J. Smith It is certified that error appears in the above-identified patent and that said Letters Patent is hereby corrected as shown below:

Column 4, line 6  
delete "substrate" and insert --guide--

Signed and Sealed this

First Day of July, 2008

JON W. DUDAS  
*Director of the United States Patent and Trademark Office*